Jan. 13, 1953 F. W. ANDERSON Plant Pat. 1,161
NECTARINE TREE
Filed March 17, 1952
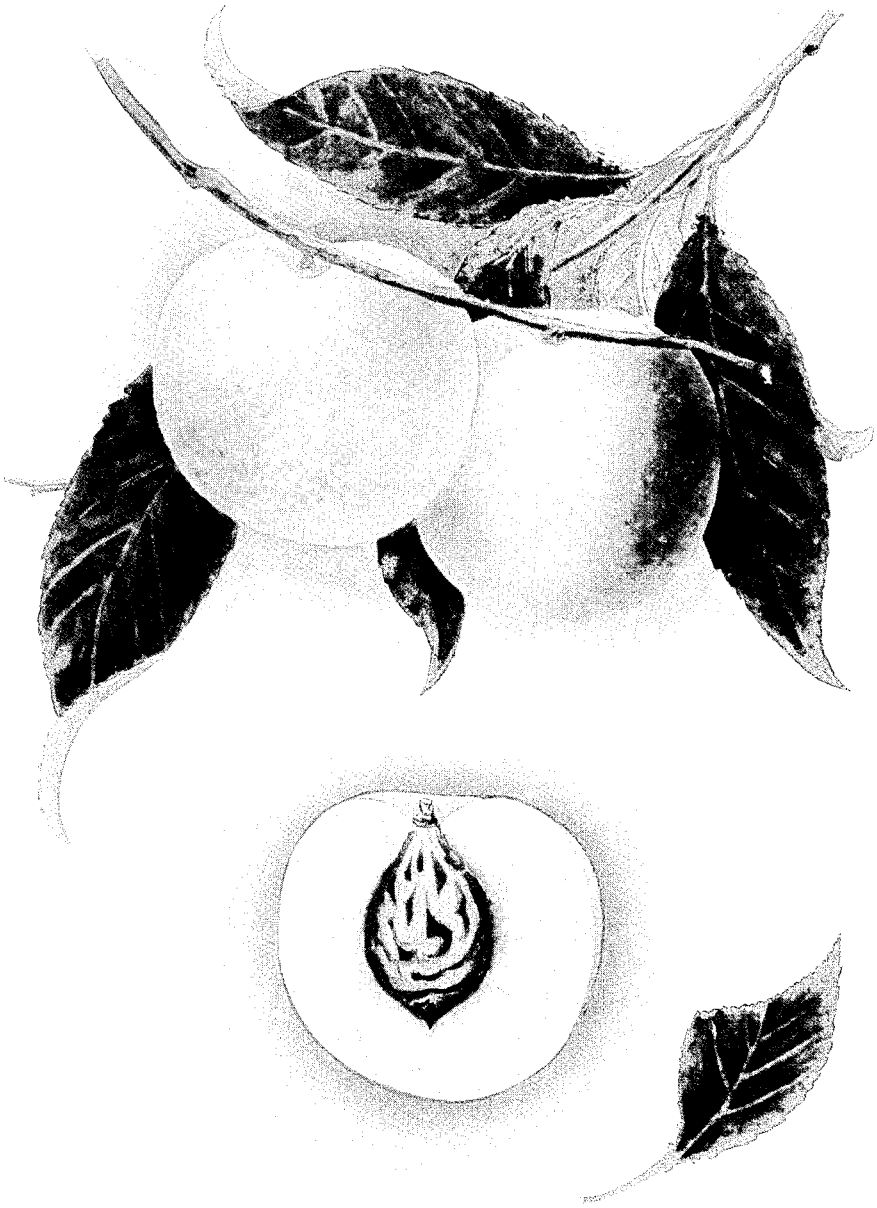
WITNESS
Addison F. Avery
INVENTOR
FREDERIC W. ANDERSON
Webster & Webster
ATTYS.

Patented Jan. 13, 1953

Plant Pat. 1,161

UNITED STATES PATENT OFFICE 1,161

NECTARINE TREE

Frederic W. Anderson, Merced, Calif., assignor to Thomas Burton Stribling, Jr., doing business as Stribling's Nurseries, Merced, Calif.

Application March 17, 1952, Serial No. 277,032

1 Claim. (Cl. 47—62)

The present invention relates to a new and distinct variety of nectarine tree which bears yellow fleshed, freestone fruit; the variety having been obtained from a plant breeding program which I have carried forward to obtain more commercially valuable nectarines.

This variety is somewhat similar to the Le Grand nectarine (United States Plant Patent No. 549), and ripens at approximately the same time; the distinctive feature being that the fruit of this variety is freestone instead of clingstone, as with the Le Grand.

This new and distinct variety of nectarine was originated by me in the following manner:

All of the flowers on a Le Grand nectarine tree were pollenized by pollen from an unnamed seedling that had resulted from a cross between the Bim nectarine (United States Plant Patent No. 575) and the Kim nectarine (United States Plant Patent No. 173).

The pits from the resulting seeds were planted in a nursery row, and later top-worked to orchard trees. The present variety was recognized in such group of nectarines as being new and distinct by reason of its being a freestone, but ripening at approximately the same time as the Le Grand nectarine, as aforesaid.

The origination of the variety, and its subsequent successful asexual reproduction by top-working onto orchard trees was conducted in the experimental orchard on my ranch near Merced, county of Merced, State of California.

By careful observation I have determined that the asexual reproductions carry forward all of the distinctive characteristics of the parent tree and its fruit.

In the drawings is shown:

A perspective view of the fruit of the new variety, together with stems and leaves;

A sectional view of one of the fruit, with the stone exposed; and,

A fragmentary elevation of one of the leaves, showing particularly the glands.

Referring now more specifically to the pomological details of this new and distinct variety of nectarine tree, the following is an outline description thereof; all major color plate identifications being by reference to Maerz and Paul Dictionary of Color:

Tree: Medium size; vigorous; spreading; open; vase formed; productive; regular bearer.

Trunk: Stocky; medium texture.

Branches: Stocky; above medium size. Lenticels—medium size.

Leaves: Large, averaging 6½″ to 7″ in length and 1¾″ to 2″ in width. Medium thick; smooth.

*Color.*—Medium green (21–L–7 to 22–L–8), lighter on under side (21–L–4).

*Margin.*—Crenate.

*Petiole.*—Medium length; medium thickness.

*Glands.*—Average number—two. Usually at base of blade. Medium size; globose. Stipules—none.

Flower buds: Medium size; short; plump.

Flowers: Large size. Full bloom about with the Elberta peach. Color—pink.

Fruit:

*Size.*—Large. Well grown specimens average from 2½″ to 3″ in both diameters.

*Form.*—Globose.

*Suture.*—Very slight, with slight, depression beyond pistil point.

*Cavity.*—Rounded, about ⅜″ in depth and ¾″ in breadth.

*Apex.*—Slightly depressed with pistil point almost lacking.

*Base.*—Rounded.

*Stem.*—Stout; adheres strongly to the stone.

*Skin.*—Above medium in thickness and toughness.

*Tendency to crack.*—Slight.

*Pubescense.*—None.

*Color.*—Yellow under-color (9–L–3) finely spotted and mottled with red (1–L–12 shading to 9–L–12); the sunny side of some fruit darkening considerably to a deep purplish-red (55–L–12).

Flesh:

*Surface of pit cavity.*—Tinged with red (4–L–6), and including brownish yellow fibers.

*Juice.*—Abundant.

*Texture.*—Very firm.

*Fibers.*—Few.

*Ripens.*—Evenly.

*Flavor.*—Delicate.

*Aroma.*—Distinct.

*Eating quality.*—Very good to best.

*Color.*—Yellow (9–K–2 to 9–L–7).

Stone: Free; parts from flesh smoothly.

*Fibers.*—Short.

*Size.*—Large. Average length, 1⅜″; average breadth, 1¼″; average thickness, ⅝″.

*Form.*—Oval.

*Base.*—Oblique.

*Hilum.*—Broad; oval.

*Apex.*—Rounded.

*Sides.*—Equal.

*Surface.*—Irregularly furrowed and pitted throughout.

*Color.*—Brown (13–A–11 to 56–L–1).

*Tendency to split.*—Slight.

Resistance to insects and diseases: Average; controlled by conventional commercial spray practices.

Keeping and eating quality: Very good, having firm flesh with uniform ripening comparable to the J. H. Hale peach.

Use: Market; dessert; culinary.

The ripening period of the present variety is late in July, being approximately the same as the Le Grand nectarine (United States Plant Patent #549) and the J. H. Hale peach (not patented); the prime distinguishing characteristics relative to the former being that here the fruit is a freestone, and additionally is more globose in shape than said Le Grand nectarine. As the J. H. Hale peach is extensively and widely grown, its ripening period—being well known—is here used as a basis of comparison.

The tree and its fruit herein described may vary in slight detail due to climatic and soil conditions under which the variety may be grown.

Having thus described my invention, I claim:

A new and distinct variety of nectarine tree substantially as described and illustrated, bearing large, firm, yellow fleshed freestone fruit with yellow skin splashed and mottled with red; such fruit ripening approximately with the clingstone Le Grand nectarine and J. H. Hale peach, and being more globose in shape than said Le Grand nectarine.

FREDERIC W. ANDERSON.

No references cited.